(12) United States Patent
Geier et al.

(10) Patent No.: US 10,526,326 B2
(45) Date of Patent: Jan. 7, 2020

(54) CRYSTALLINE FORM AND ACETIC ACID ADDUCTS OF PALBOCICLIB

(71) Applicant: RATIOPHARM GMBH, Ulm (DE)

(72) Inventors: Jens Geier, Hayingen (DE); Wolfgang Albrecht, Ulm (DE); Ludovic Coutable, Ulm (DE); Manfred Erdmann, Neu-Ulm (DE)

(73) Assignee: ratiopharm GmbH, Ulm (DE)

( * ) Notice: Subject to any disclaimer, the term of this patent is extended or adjusted under 35 U.S.C. 154(b) by 0 days.

(21) Appl. No.: 15/749,100

(22) PCT Filed: Jul. 12, 2016

(86) PCT No.: PCT/EP2016/066557
§ 371 (c)(1),
(2) Date: Jan. 30, 2018

(87) PCT Pub. No.: WO2017/021111
PCT Pub. Date: Feb. 9, 2017

(65) Prior Publication Data
US 2018/0222903 A1 Aug. 9, 2018

(30) Foreign Application Priority Data
Aug. 5, 2015 (EP) ..................... 15179779

(51) Int. Cl.
| | | |
|---|---|---|
| *A61K 31/519* | (2006.01) | |
| *C07D 487/04* | (2006.01) | |
| *C07D 471/04* | (2006.01) | |
| *A61P 35/00* | (2006.01) | |
| *B01D 9/00* | (2006.01) | |

(52) U.S. Cl.
CPC ............ *C07D 471/04* (2013.01); *A61P 35/00* (2018.01); *B01D 9/005* (2013.01)

(58) Field of Classification Search
CPC ............................. A61K 31/519; C07D 487/04
USPC ....................... 514/264.11; 544/279
See application file for complete search history.

(56) References Cited

U.S. PATENT DOCUMENTS

2018/0319790 A1  11/2018  Fan et al.

FOREIGN PATENT DOCUMENTS

| WO | 2003062236 A2 | 7/2003 |
|---|---|---|
| WO | 2005005426 A2 | 1/2005 |
| WO | 2008032157 A2 | 3/2008 |
| WO | 2014128588 A2 | 8/2014 |
| WO | 2016156070 A2 | 10/2016 |
| WO | 2017145054 A2 | 8/2017 |
| WO | 2018007927 A2 | 1/2018 |
| WO | 2018073574 A2 | 4/2018 |

OTHER PUBLICATIONS

Duan, et al. 2016 Org. Process Res. Dev. 20(7):1191-1202 (May 12, 2016).
Maloney, et al. 2016 Org. Process Res. Dev. 20(7):1203-1216 (May 12, 2016).
Chekal, et al. 2016 Org. Process Res. Dev. 20(7):1217-1226 (Jun. 9, 2016).
"Crystalline Form of Palbociclib" IP.com No. IPCOM000246406D (Jun. 6, 2016).
"Process for the Preparation of Palbociclib Crystalline Forms" IP.com No. IPCOM000246804D (Jul. 1, 2016).

*Primary Examiner* — Douglas M Willis
(74) *Attorney, Agent, or Firm* — Milstein Zhang & Wu LLC

(57) ABSTRACT

The present invention relates to an adduct of palbociclib, a method of preparing the preparing the same, and a pharmaceutical composition comprising the same. More particularly, the invention provides a crystalline form of palbociclib, a method of preparing the same, as well as a pharmaceutical composition comprising the same.

7 Claims, 12 Drawing Sheets

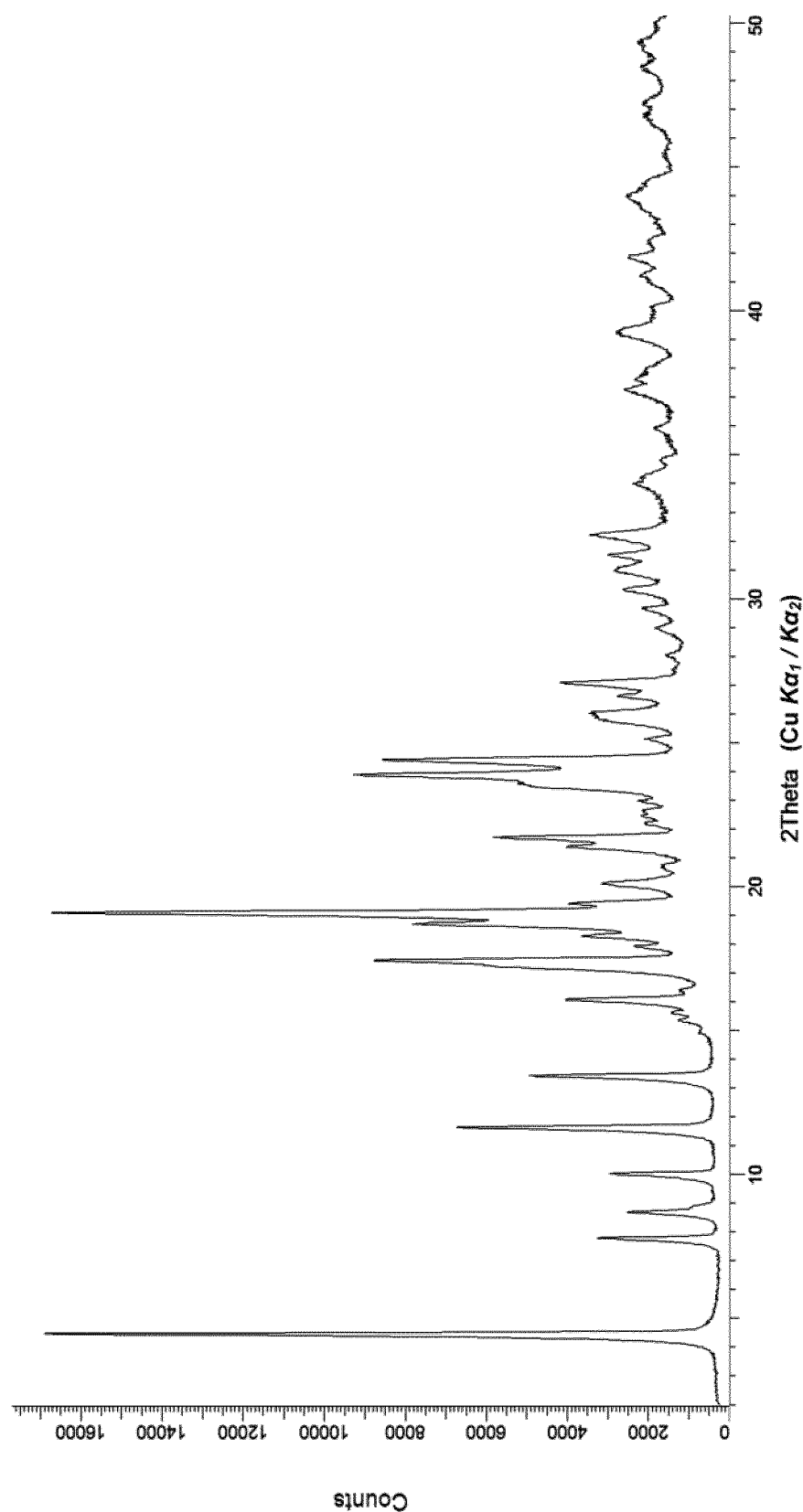
Figure 1: X-ray powder diffractogram of palbociclib acetic acid adduct Form 1

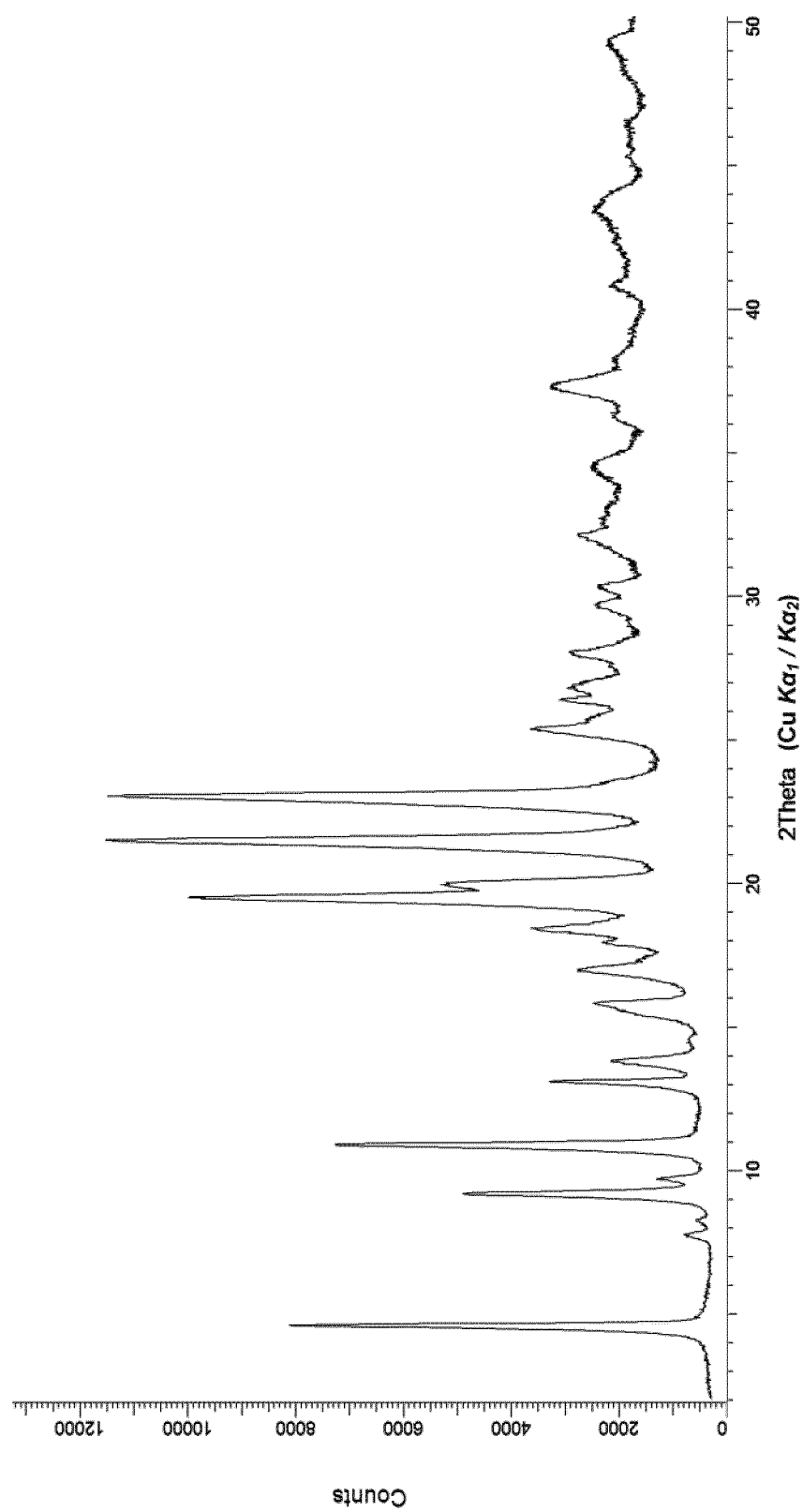
Figure 2: X-ray powder diffractogram of palbociclib acetic acid adduct Form 2

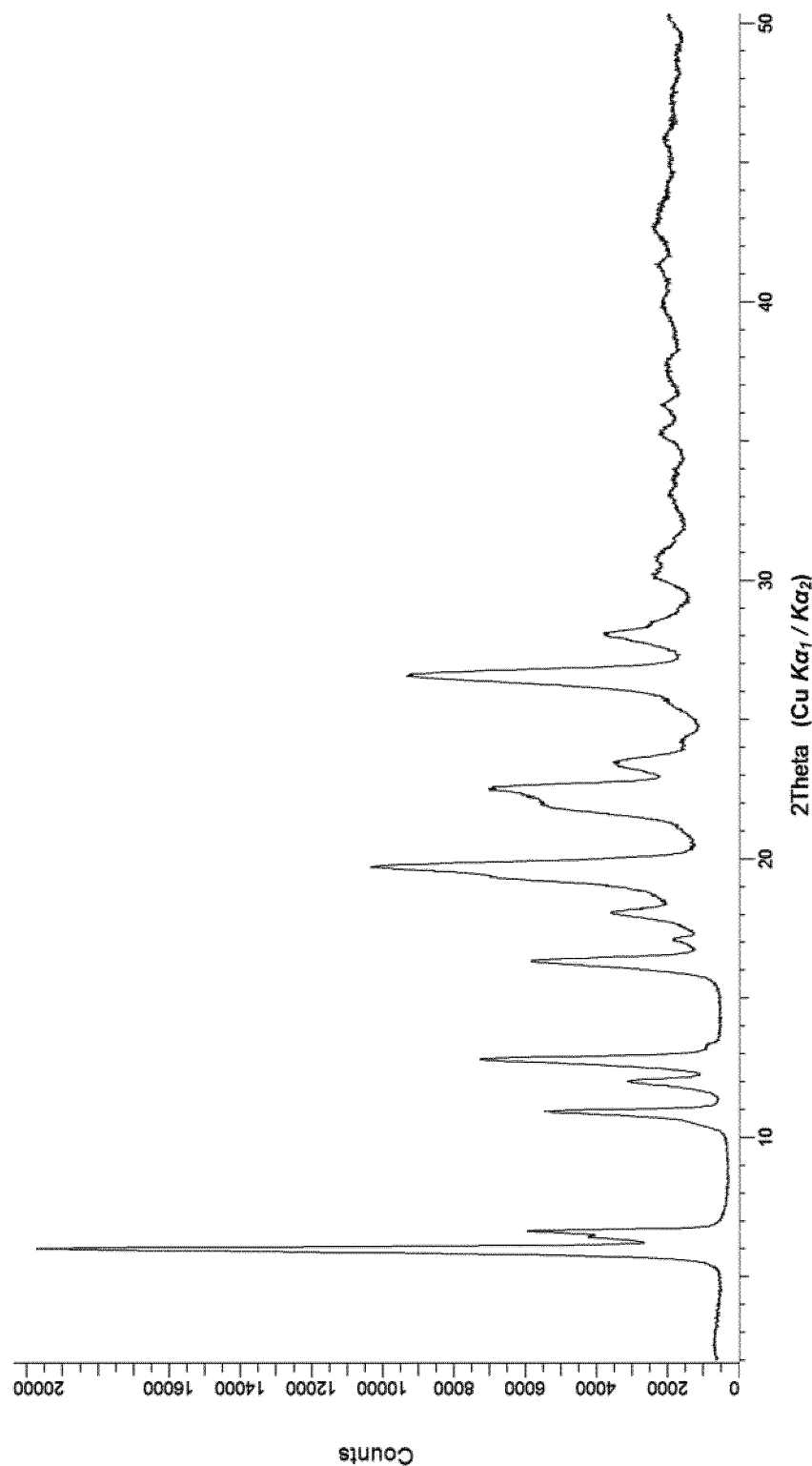
Figure 3: X-ray powder diffractogram of present palbociclib in crystalline form

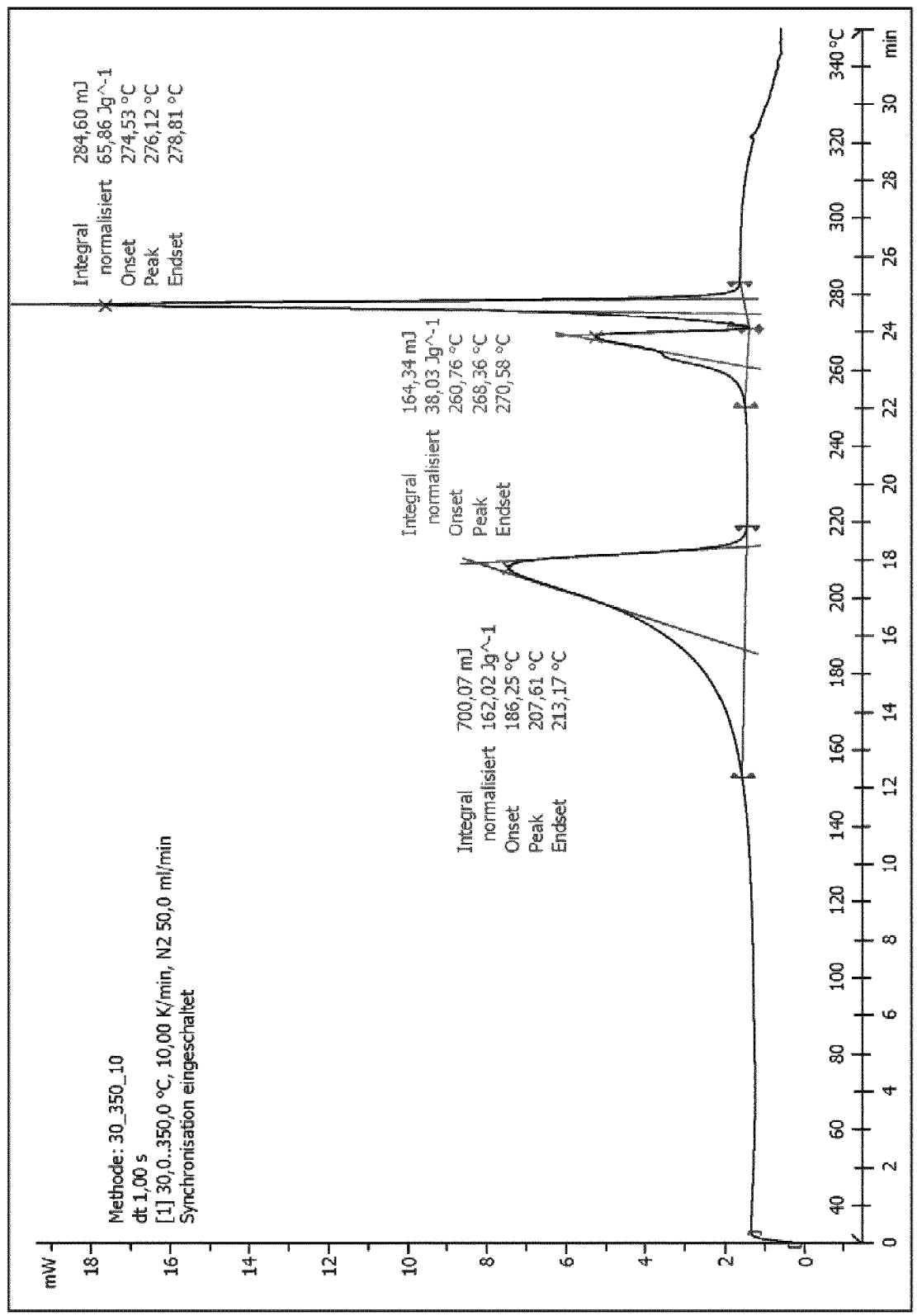
Figure 4: DSC thermogram of palbociclib acetic acid adduct Form 1

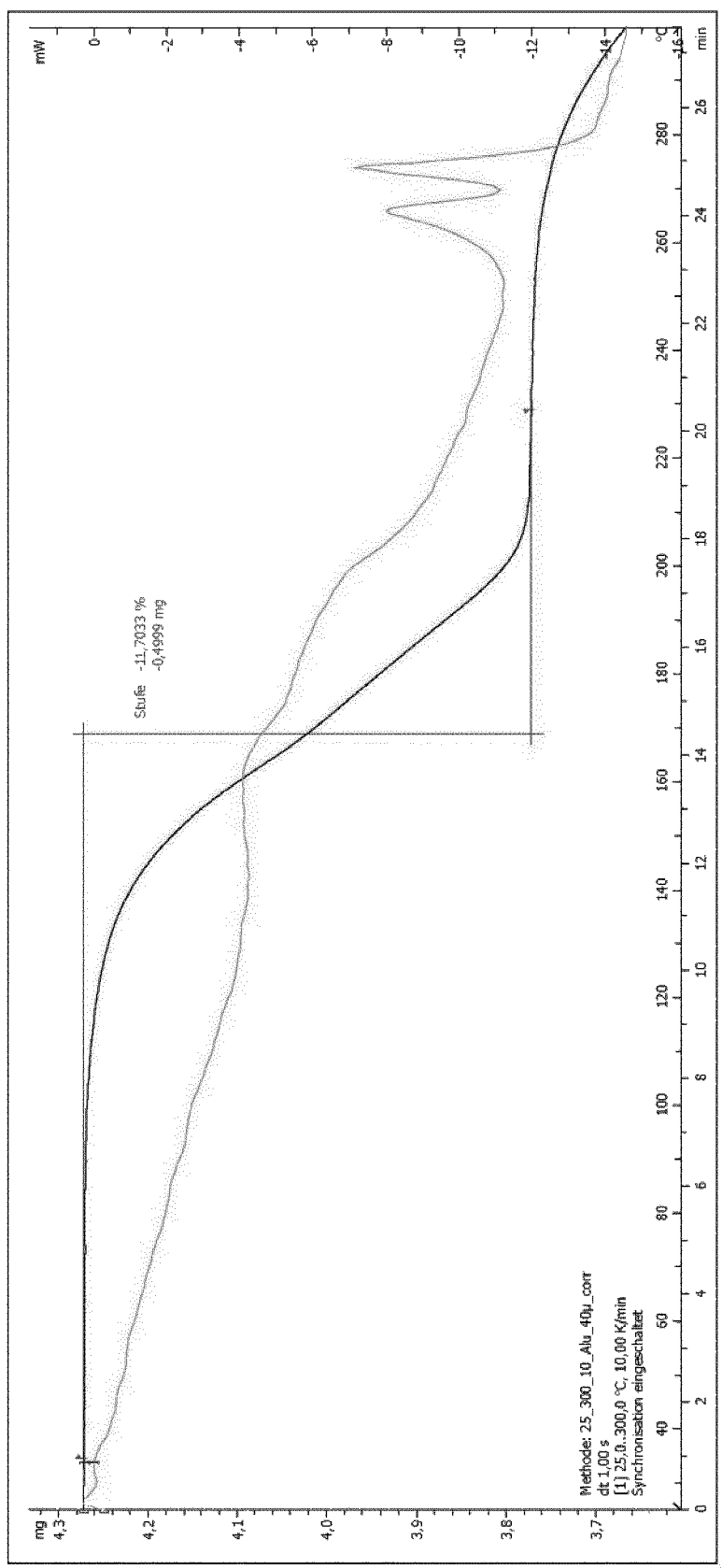
Figure 5: TGA thermogram of palbociclib acetic acid adduct Form 1

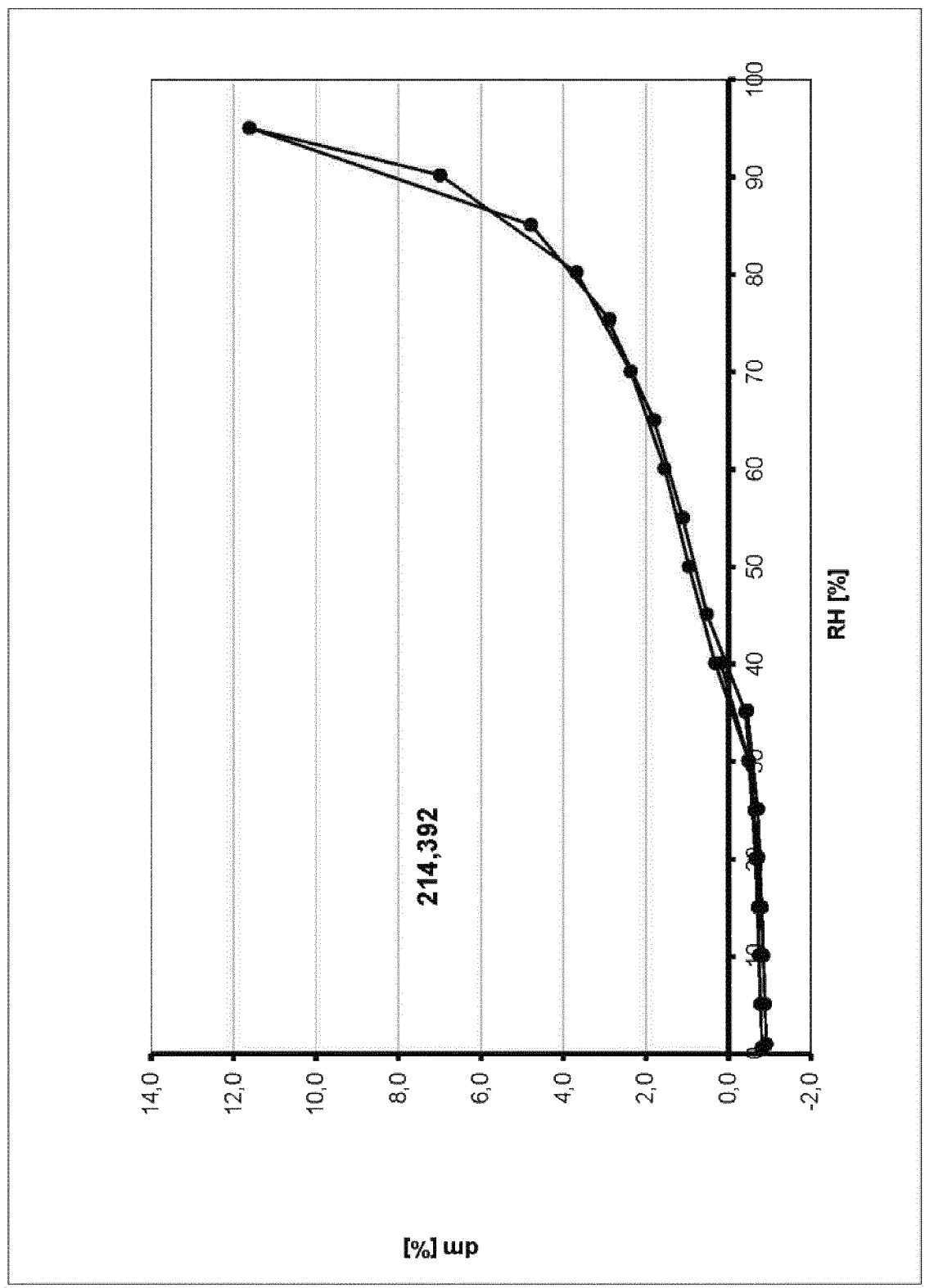
Figure 6: DVS examination of palbociclib acetic acid adduct Form 1

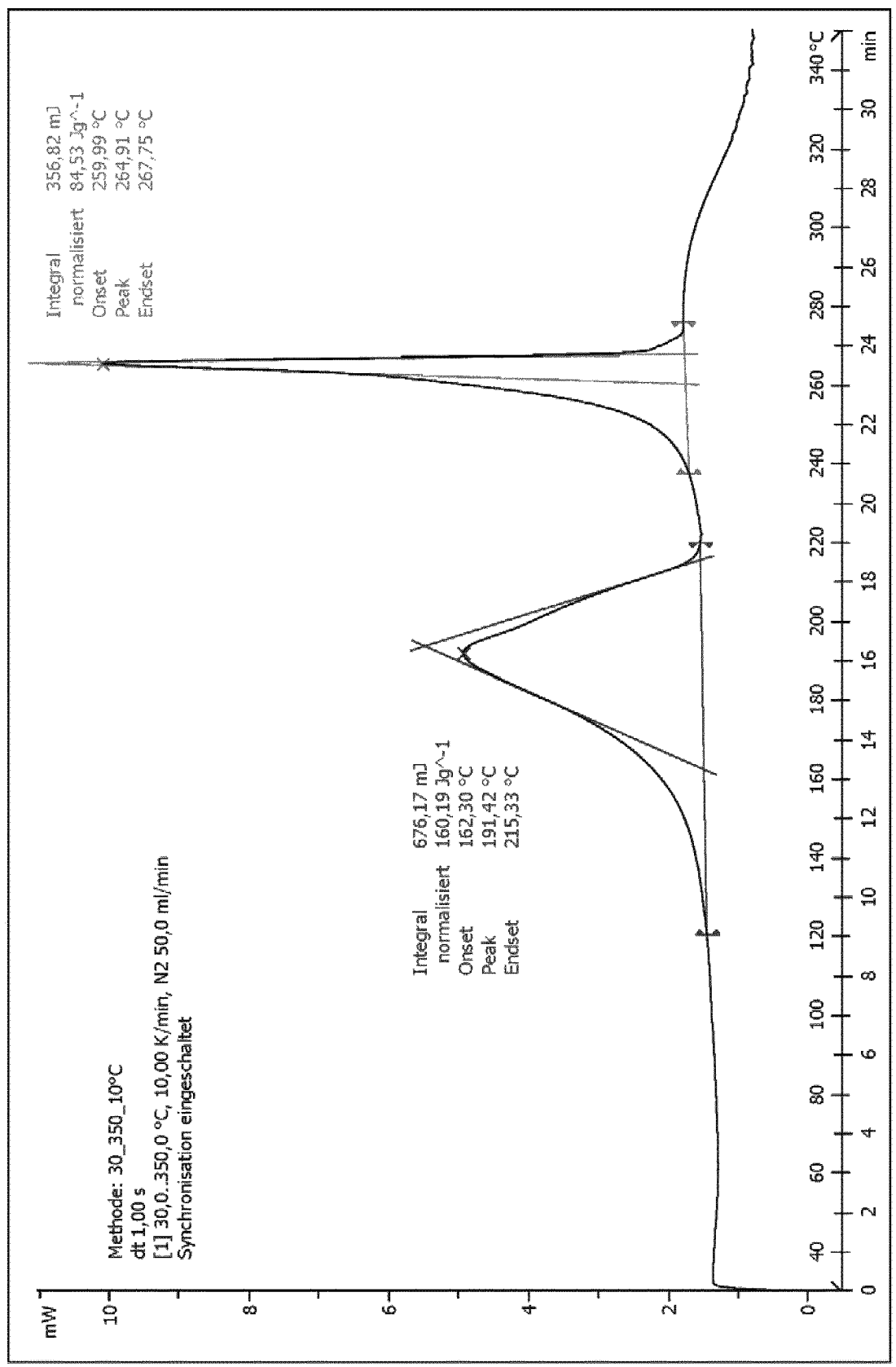
Figure 7: DSC thermogram of palbociclib acetic acid adduct Form 2

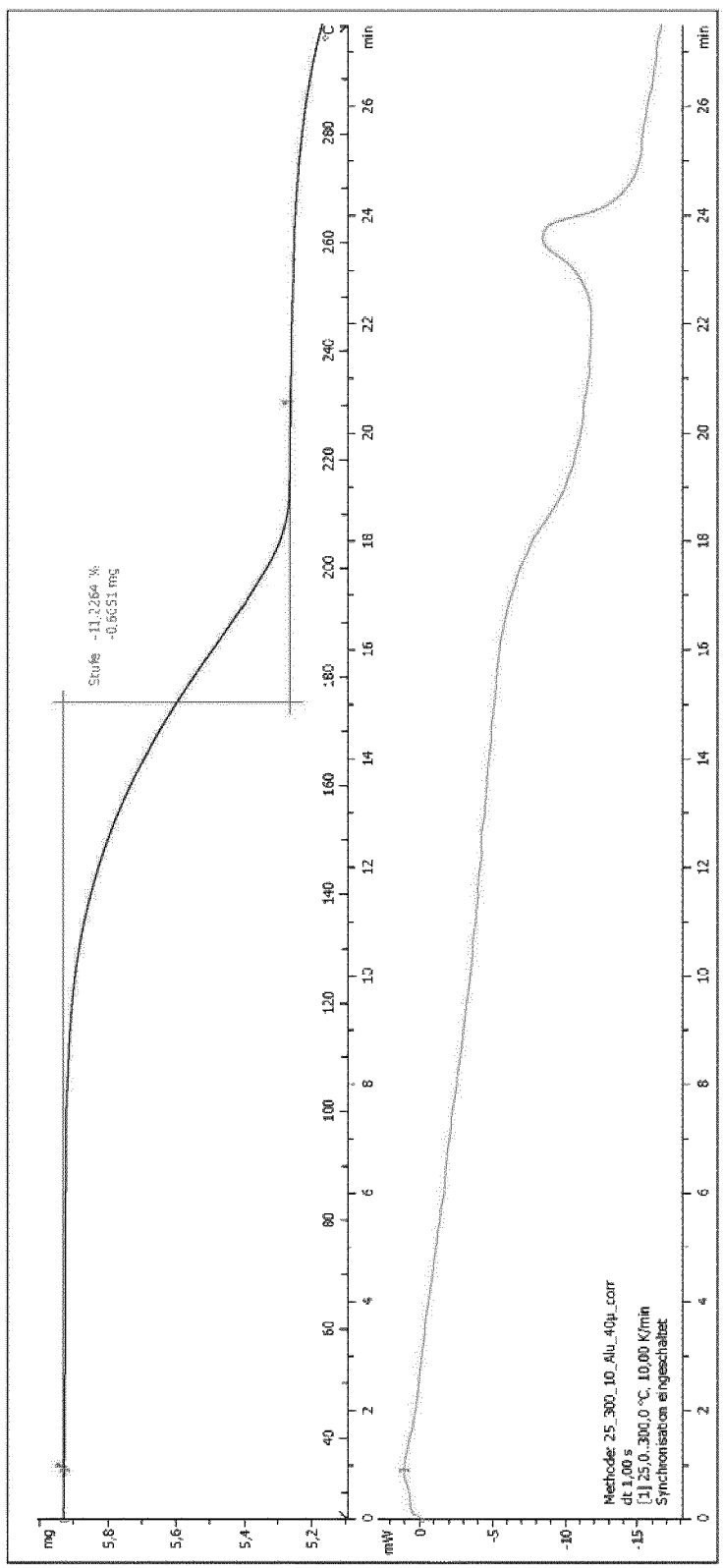
Figure 8: TGA thermogram of palbociclib acetic acid adduct Form 2

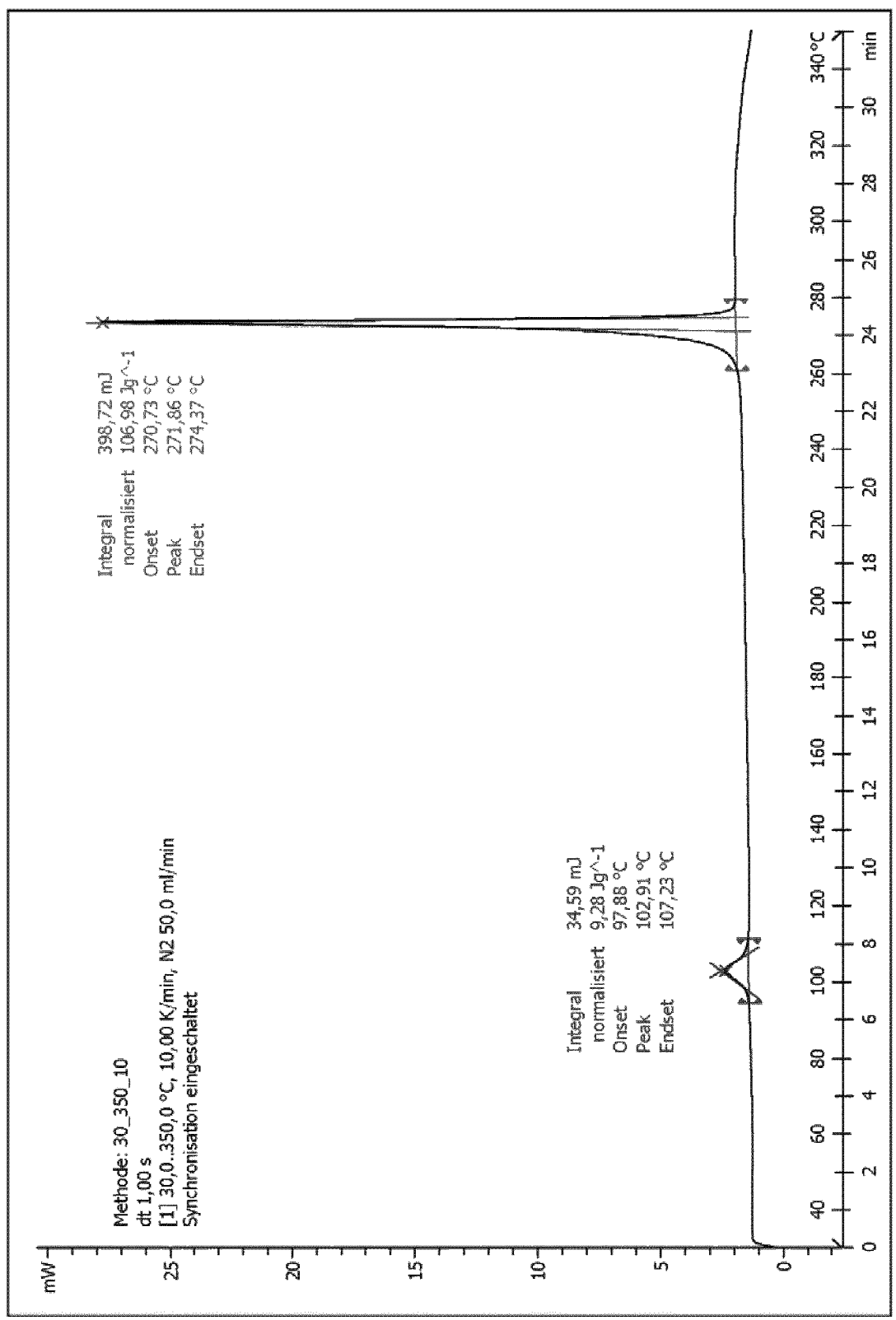
Figure 9: DSC thermogram of present palbociclib in crystalline form

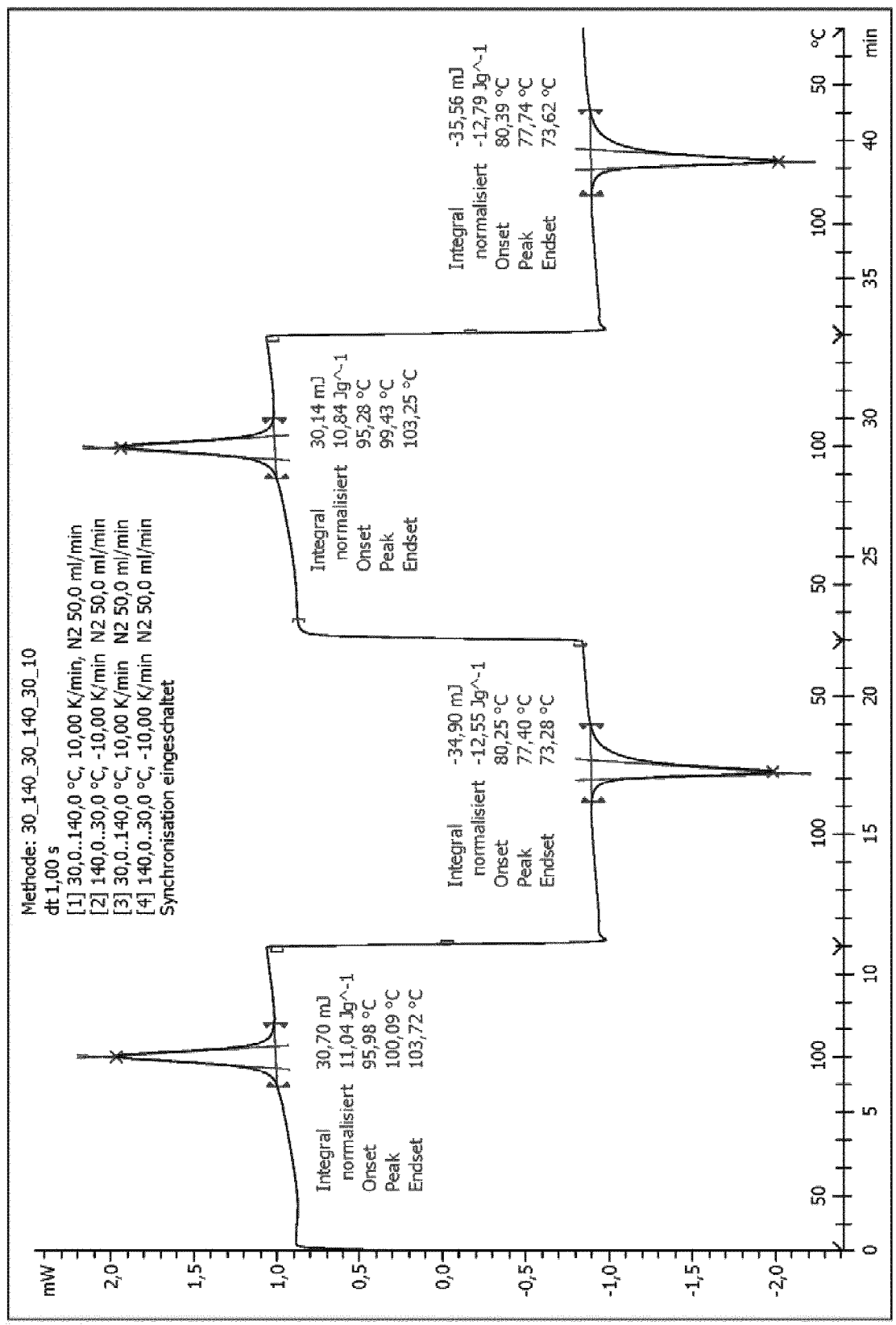
Figure 10: Cyclic DSC thermogram of present palbociclib in crystalline form

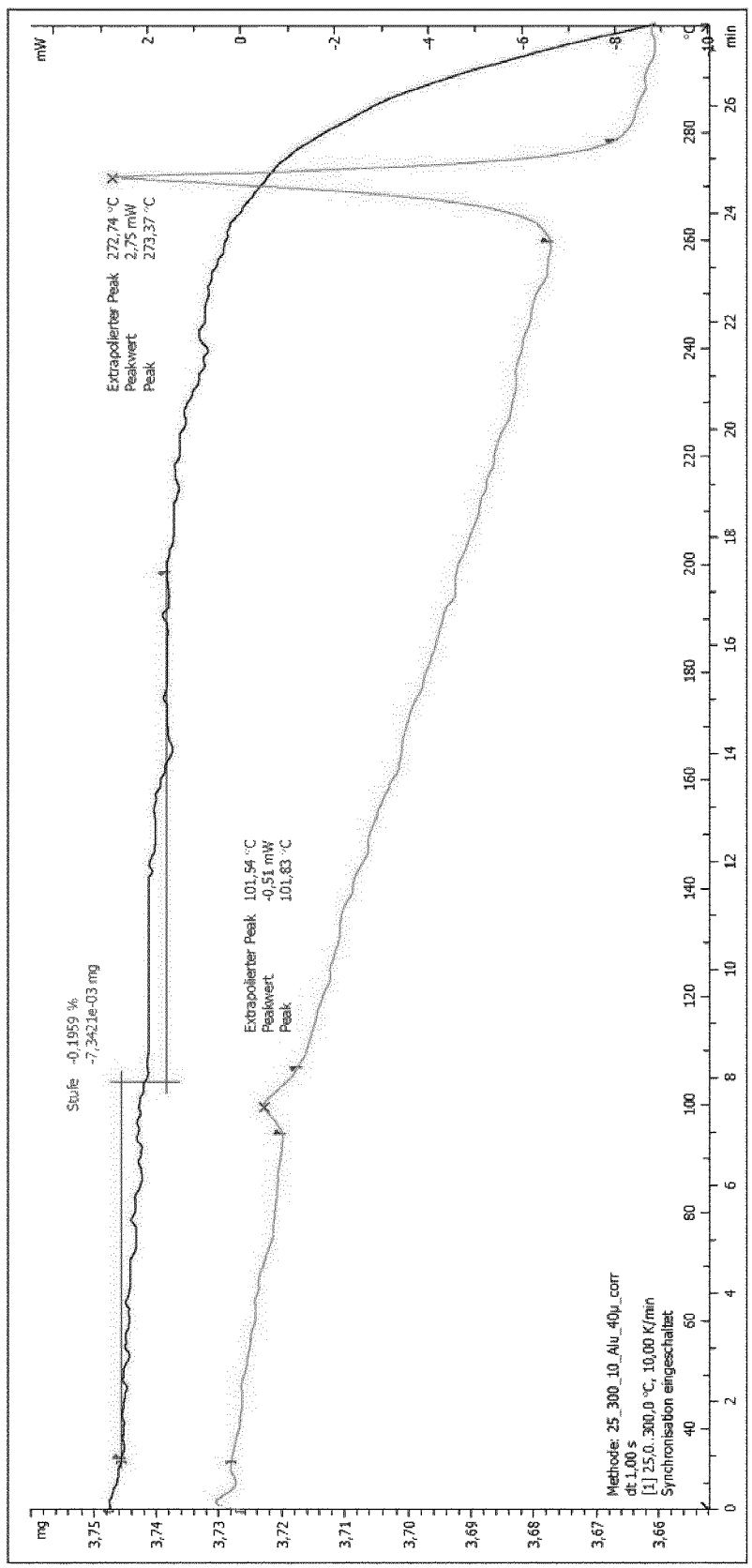
Figure 11: TGA thermogram of present palbociclib in crystalline form

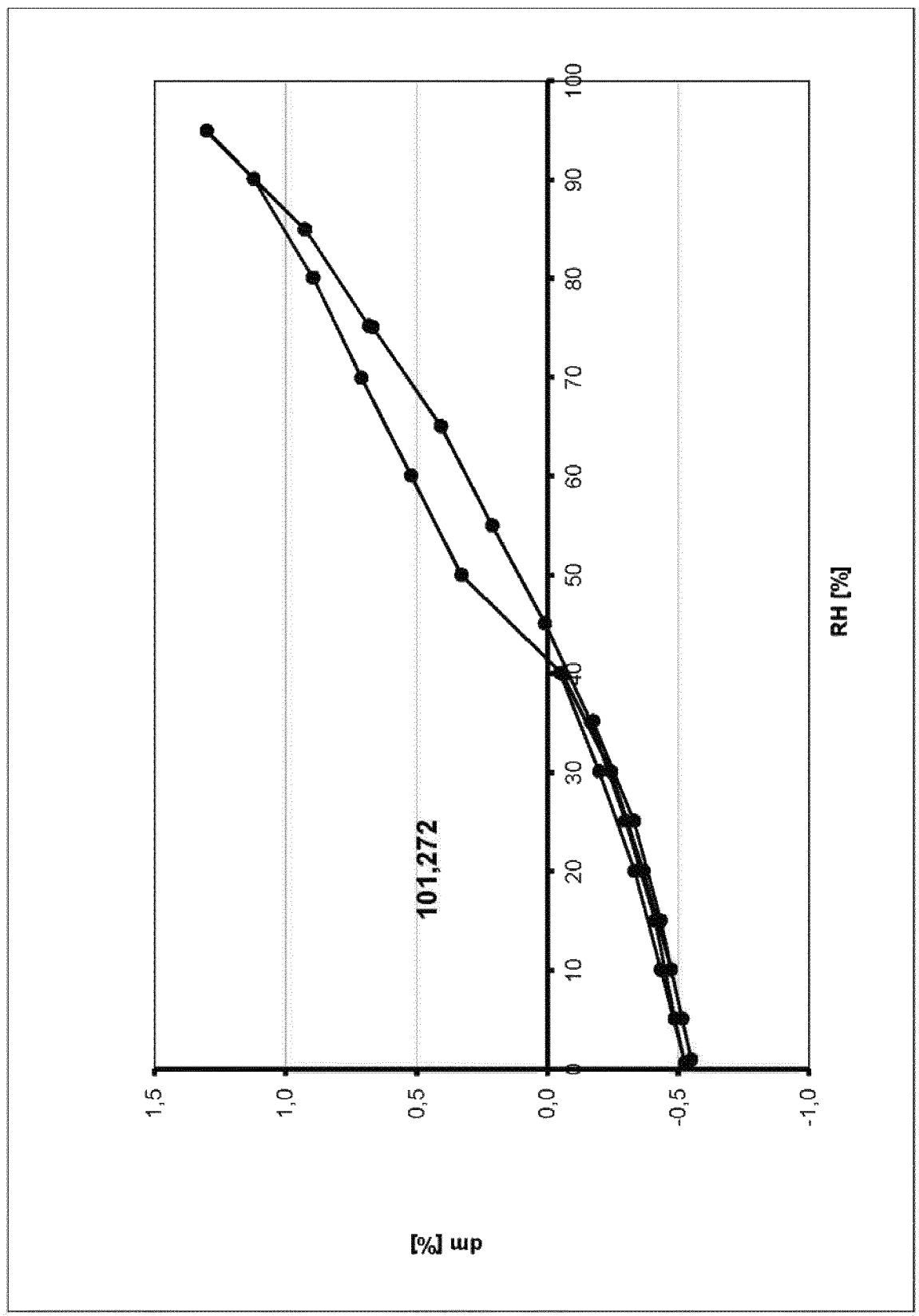
Figure 12: DVS examination of present palbociclib in crystalline from

CRYSTALLINE FORM AND ACETIC ACID ADDUCTS OF PALBOCICLIB

TECHNICAL FIELD OF THE INVENTION

The present invention relates to an adduct of palbociclib, a method of preparing the same, as well as a pharmaceutical composition comprising the same.

BACKGROUND OF THE INVENTION

The IUPAC name of palbociclib is 6-acetyl-8-cyclopentyl-5-methyl-2-{[5-(1-piperazinyl)-2-pyridinyl]amino}pyrido[2,3-d]pyrimidin-7(8H)-one.

Palbociclib is represented by the following chemical structure according to Formula (I):

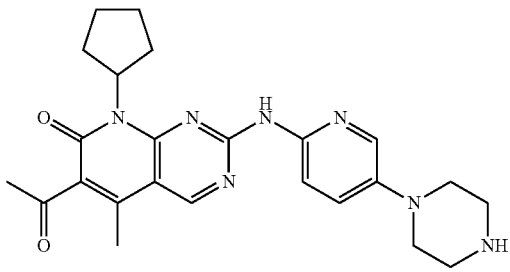 [SMILES: CC(=O)c1c(C)c2cnc(Nc3ccc(N4CCNCC4)cn3)nc2n(C2CCCC2)c1=O]

Formula (I)

Palbociclib (also known as PD-0332991 or 6-acetyl-8-cyclopentyl-5-methyl-2-(5-piperazin-1-yl-pyridin-2ylamino)-8H-pyrido[2,3-d]pyrimidin-7-one) is a selective inhibitor of the cyclin-dependent kinases CDK4 and CDK6. The active pharmaceutical ingredient is administered in the treatment of ER-positive and HER2-negative breast cancer. It is reported to be used in combination with a further drug (letrozole) for patients with estrogen receptor-positive advanced breast cancer.

The active pharmaceutical ingredient palbociclib is known from WO 03/062236 A1.

In WO 2014/128588 A1 two solid forms of palbociclib are discussed, which are denominated as Form A and Form B. According to said application Form A can be used in pharmaceutical formulations, but only if it is prepared in a particle size distribution above specified thresholds, because of the strong electrostatic charging of smaller particles.

With regard to the Form B a X-ray powder diffractogram and $^{13}$C CPMAS spectrum was disclosed. However, no further information is given, neither to its synthesis nor to its properties. Thus, the alleged Form B cannot be regarded as being enabled by the above-mentioned application.

Palbociclib (Form A) is reported to be a yellow to orange powder with pKa of 7.4 (the secondary piperazine nitrogen) and 3.9 (the pyridine nitrogen). Palbociclib in form of the free base is allegedly practically insoluble in water. However, when subjected to acidic conditions, such as at or below pH 4, palbociclib allegedly shows good solubility.

One option to enhance the solubility is the formation of a palbociclib base or acid addition salt. Known salts like hydrochloride, dihydrochloride, and 2-hydroxyethyl-sulfonate (WO 2005/005426 A1) show good water solubility. However, they are reported to have certain disadvantages. For example, the hydrochloride of palbociclib features low crystallinity, and the dihydrochloride of palbociclib is hygroscopic. Further the 2-hydroxyethylsulfonate of palbociclib raises potential safety problems (because the permissible daily exposure limit for the anion will likely be exceeded in therapeutic applications).

Consequently, there is still a need for forms of palbociclib in form of solid state having superior properties. Hence, it was an object of the present invention to overcome the drawbacks of the above-mentioned prior art.

SUMMARY OF THE INVENTION

In particular, it was an object of the present invention to provide a form of palbociclib showing a better solubility in water and/or in organic solvents than palbociclib Form A. Further, the new form should have superior properties, e.g. in view of hygroscopicity, processability and/or stability.

Additionally, palbociclib should be provided in a form being toxicologically uncritical.

BRIEF DESCRIPTION OF THE DRAWINGS

FIG. 1: X-ray powder diffractogram of palbociclib acetic acid adduct Form 1.

FIG. 2: X-ray powder diffractogram of palbociclib acetic acid adduct Form 2.

FIG. 3: X-ray powder diffractogram of present palbociclib in crystalline form.

FIG. 4: DSC thermogram of palbociclib acetic acid adduct Form 1.

FIG. 5: TGA thermogram of palbociclib acetic acid adduct Form 1.

FIG. 6: DVS examination of palbociclib acetic acid adduct Form 1.

FIG. 7: DSC thermogram of palbociclib acetic acid adduct Form 2.

FIG. 8: TGA thermogram of palbociclib acetic acid adduct Form 2.

FIG. 9: DSC thermogram of present palbociclib in crystalline form.

FIG. 10: Cyclic DSC thermogram of present palbociclib in crystalline form.

FIG. 11: TGA thermogram of present palbociclib in crystalline form.

FIG. 12: DVS examination of present palbociclib in crystalline from.

DETAILED DESCRIPTION OF THE INVENTION

According to the present invention, the above objectives are unexpectedly achieved by a palbociclib acetic acid adduct.

Thus, a subject of the invention is palbociclib acetic adduct. According to the invention, an adduct refers to a product which is composed of two or more, preferably two components, wherein no side-products are formed when reacting the components to the adduct. Such an adduct can be considered a distinct molecular species. Adducts may be formed via the formation of covalent bonded molecules, such as Lewis acid (electron pair acceptor) and Lewis base (electron pair donor), via agglomeration of a solvent to form a solvate or the formation of an ionic bond to form a salt. In a preferred embodiment the adduct is a solvate. In a preferred embodiment the adduct is a salt.

In a preferred embodiment of the invention palbociclib and acetic acid are present in a palbociclib acetic acid adduct in molar ratio between 1:1.5 and 1.5:1, preferably between 1:1.25 and 1.25:1. It turned out that with the above ratio a stable palbociclib acetic acid adduct can be formed. The adduct of the present invention further preferably shows an advantageous hygroscopicity.

The palbociclib acetic acid adduct can be preferably present in crystalline form.

A crystal form may be referred to herein as being characterized by data selected from two or more different data groupings, for example by a powder XRD pattern, having a group of specific peaks or by a powder XRD pattern as shown in a figure depicting a diffractogram, or by "a combination thereof" (or "combinations thereof" or "any combination thereof"). These expressions, e.g. "any combination thereof", contemplate that the skilled person may characterize a crystal form using any combination of the recited characteristic analytical data. For example, the skilled person may characterize a crystal form using a group of three, four or five characteristic powder XRD peaks and supplement this characterization with one or more additional feature(s) observed in the powder X-ray diffractogram, e.g., an additional peak, a characteristic peak shape, a peak intensity or even the absence of a peak at some position in the powder XRD pattern. Alternatively, the skilled person may in some instances characterize a crystal form using a group of three, four or five characteristic powder XRD peaks and supplement that characterization with one or more additional feature(s) observed by using another analytical method, for example using one or more characteristic peaks in a solid state IR spectrum, solid state NMR or characteristics of the DSC thermogram of the crystal form that is being characterized.

Unless otherwise indicated, XRPD peaks are recorded using copper $K\alpha_1/K\alpha_2$ radiation with a wavelength of 1.54187 Å (weighted mean of Cu $K\alpha_1$ and Cu $K\alpha_2$). Further, unless indicated otherwise, XRPD peaks are reported as degrees 2θ values with a standard error of ±0.2 degrees 2θ.

A crystal form may be referred to herein as being characterized by graphical data "as depicted in" a particular figure. Such data include for example powder X-ray diffractograms. The skilled person will understand that such graphical representation of data may be subject to small variations, e.g. in peak relative intensities and peak positions, due to factors such as variations in instrument response and variations in sample concentration and purity, which are well-known to the skilled person. Nonetheless, the skilled person would readily be capable of comparing the graphical data in the figures herein with graphical data generated for an unknown crystal form, and confirm as to whether the two sets of graphical data characterize the same crystal form or two different crystal forms.

In a preferred embodiment palbociclib acetic acid adduct can preferably have characteristic X-ray powder diffraction peaks at 8.7, 10.0, 11.6, 13.4 and 19.1 degrees 2θ (±0.2 degrees 2θ). That form of palbociclib acetic acid adduct is hereinafter referred to as polymorphic Form 1 of palbociclib acetic acid adduct.

In a preferred embodiment the palbociclib acetic acid adduct Form 1 can be characterized by one or more further XRPD diffraction peak(s) at 4.5, 7.8, 16.1, 17.4 and/or 21.7 degrees 2θ (±0.2 degrees 2θ).

In an alternatively further preferred embodiment of the present invention palbociclib acetic acid adduct Form 1 can be characterized by the XRPD diffraction peak(s) at degrees 2θ±0.2 degrees 2θ (intensity %): 4.5 (100), 7.8 (18), 8.7 (13), 8.8 (4), 10.0 (15), 11.6 (38), 13.4 (27), 14.9 (1), 15.4 (4), 15.6 (5), 16.1 (20), 16.4 (2), 17.3 (32), 17.4 (48), 17.9 (8), 18.3 (16), 18.7 (41), 19.1 (95), 19.4 (17), 20.1 (12), 20.7 (3), 21.4 (17), 21.7 (27), 22.2 (4), 22.5 (5), 22.6 (4), 23.0 (5), 23.6 (23), 23.9 (48), 24.4 (44), 25.1 (4), 25.9 (11), 26.6 (9), 27.1 (17), 28.0 (2), 29.0 (4), 29.6 (5), 30.3 (8), 31.0 (9), 31.5 (10), 32.2 (13), 34.0 (6), 34.8 (2), 35.9 (3), 37.3 (7), 37.6 (5), 39.3 (8), 41.2 (5), 41.9 (6), 42.4 (3) and 44.0 (6).

An XRPD diffraction pattern of a preferred embodiment of the palbociclib acetic acid adduct Form 1 of the present invention is shown in FIG. 1.

In a preferred embodiment of the invention in palbociclib acetic acid adduct Form 1 comprises palbociclib and acetic acid in molar ratio between 1:1.1 and 1.1:1, in particular about 1:1.

In a preferred embodiment palbociclib acetic acid adduct can preferably have characteristic X-ray powder diffraction peaks at 9.2, 10.9, 13.1, 13.8 and 23.0 degrees 2θ (±0.2 degrees 2θ). That form of palbociclib acetic acid adduct is hereinafter referred to as polymorphic Form 2 of palbociclib acetic acid adduct.

In a preferred embodiment the palbociclib acetic acid adduct Form 2 can be characterized by one or more further XRPD diffraction peak(s) at 4.6, 17.0, 19.5, 20.0 and/or 21.5 degrees 2θ (±0.2 degrees 2θ).

In an alternatively further preferred embodiment of the present invention palbociclib acetic acid adduct Form 2 can be characterized by the XRPD diffraction peak(s) at degrees 2θ±0.2 degrees 2θ (intensity %): 4.6 (75), 7.8 (4), 8.3 (2), 9.2 (44), 9.7 (8), 10.9 (67), 13.1 (27), 13.8 (15), 14.5 (1), 15.8 (17), 17.0 (19), 17.3 (6), 18.0 (12), 18.4 (24), 19.5 (85), 20.0 (40), 21.5 (100), 23.0 (99), 25.4 (22), 25.7 (11), 26.4 (16), 26.8 (13), 28.0 (12), 29.7 (8), 30.3 (7), 32.1 (10), 34.6 (8), 36.3 (4), 37.3 (15), 38.3 (4), 40.8 (5), 43.5 (8), 45.3 (2), 46.4 (2) and 49.3 (6).

An XRPD diffraction pattern of a preferred embodiment of the palbociclib acetic acid adduct Form 2 of the present invention is shown in FIG. 2.

The palbociclib acetic acid adduct of the present invention shows an unexpectedly enhanced solubility in water compared to palbociclib Form A. In addition present palbociclib acetic acid adduct shows a good crystallinity and/or an advantageous hygroscopicity compared to common palbociclib acid additions salts, such as palbociclib hydrochloride or palbociclib dihydrochloride. Moreover, palbociclib acetic acid adduct is regarded as toxicologically uncritical. Furthermore, shelf-life is advantageous.

A further subject of the present invention is a process for preparing palbociclib acetic acid adduct according to the present invention, comprising the steps of
a) providing palbociclib
b) dissolving palbociclib from step a) in aqueous acetic acid
c) isolating palbociclib acetic acid adduct.

In step a) palbociclib, preferably palbociclib in form of its free base, for example palbociclib Form A as described in WO 2014/12858 A1, is provided. Palbociclib in form of its free base can preferably refer to solvates and hydrates thereof.

In step b) palbociclib from step a) is dissolved, preferably completely dissolved, in aqueous acetic acid. It is preferred that the aqueous acetic acid is a mixture of water and glacial acetic acid. Water and glacial acetic acid can preferably be mixed in a volume ratio of 1:3 to 3:1, more preferably of 1:2 to 2:1, even more preferably of 1:1.5 to 1.5:1, in particular about 1:1.

It is further preferred that step b) is carried out under mechanical movement, such as stirring. In a preferred embodiment step b) includes stirring for 0.5 to 6 hours, preferably 1 to 2 hours.

Step b) can preferably be carried out at 23° C. (room temperature). Alternatively step b) can be carried out under an elevated temperature. An elevated temperature corresponds to a temperature being between 23° C. and the boiling point of the aqueous acetic acid. In case the dissolution is raised to an elevated temperature, said solution can preferably be cooled again to 23° C.

Step c) of isolating palbociclib acetic acid adduct can preferably comprise filtering the solution of step b), for example through a folded filter to remove undissolved solid.

Further step c) can preferably comprise removing the solvent(s).

In a preferred embodiment removing the solvent(s) can be carried out under an elevated temperature of 50° C. to 100° C., preferably about 90° C. Alternatively or additionally, the removing can preferably be carried out under reduced pressure of from 50 to 200 mbar, in particular 70 to 150 mbar. Drying can be preferably carried out for example by a rotary evaporator at 85 mbar and 90° C.

The resulting solid can preferably be triturated and subsequently preferably be further dried. Drying of the solid can be conducted under the same conditions as described above. Drying of the solid can preferably last for 2 to 8 hours. The resulting product is palbociclib acetic acid adduct Form 1.

In an alternatively preferred embodiment removal of the solvent(s) can be carried out under an elevated temperature of 25° C. to 65° C., preferably about 50° C. Alternatively or additionally, removal can preferably be carried out under reduced pressure of from 30 to 100 mbar, in particular 50 to 80 mbar. Drying can be preferably carried out for example by a rotary evaporator at 60 mbar and 50° C.

The resulting solid can preferably be triturated and subsequently preferably be further dried. Drying of the solid can be carried out under at temperature of 20° C. to 35° C., preferably about 23° C. Alternatively or additionally, the drying can preferably be carried out under reduced pressure of from 0.0001 to 0.01 mbar, in particular 0.0010 mbar. Drying of the solid can preferably last for 2 to 18 hours.

Alternatively or additionally drying of the solid can be carried out under at a temperature of 60° C. to 90° C., preferably about 80° C., and under reduced pressure of from 1 to 50 mbar, preferably from 2 to 30 mbar, in particular from 5 to 15 mbar. Drying of the solid can preferably last for 2 to 36 hours, preferably for 20 to 25 hours. The resulting product is palbociclib acetic acid adduct Form 2.

As can be seen from the above, palbociclib acetic acid adduct, especially Form 1 as well as Form 2, are easily available by a process without the use of complex, time- and cost-intensive process steps.

A further subject of the present invention is palbociclib in crystalline form having characteristic X-ray powder diffraction peaks at 6.0, 10.9, 12.8, 16.3 and/or 19.7 degrees 2θ (±0.2 degrees 2θ).

In a preferred embodiment, the palbociclib in crystalline form according to the present invention can be characterized by one or more further XRPD diffraction peak(s) at 6.6, 19.4, 22.0, 22.5, and/or 26.6 degrees 2θ (±0.2 degrees 2θ).

In a further preferred embodiment of the present invention palbociclib in crystalline form can be characterized by the XRPD diffraction peak(s) at degrees 2θ±0.2 degrees 2θ (intensity %): 6.0 (100), 6.4 (19), 6.6 (29), 10.9 (25), 12.0 (13), 12.8 (34), 16.3 (26), 17.1 (5), 18.1 (13), 19.4 (30), 19.7 (47), 22.0 (22), 22.5 (29), 23.4 (12), 24.2 (3), 26.6 (40), 28.1 (12), 30.2 (5) and 30.8 (4).

An XRPD diffraction pattern of palbociclib in crystalline form according to the present invention is shown in FIG. 3.

The palbociclib in crystalline form adduct of the present invention shows an unexpectedly enhanced solubility in organic solvents compared to palbociclib Form A. Thus, for a possible amorphisation an advantageously smaller amount of organic solvent is required.

Further, the present invention relates to a method for preparing palbociclib of the present invention comprising the steps of
   a') providing palbociclib
   b') dissolving palbociclib from step a') in aqueous acetic acid
   c') optionally isolating palbociclib acetic acid adduct
   d') optionally dissolving palbociclib acetic acid adduct from step c') in water
   e') adding the solution from step b') or the solution from step d') to an aqueous, alkaline solution
   f') isolating palbociclib in crystalline form.

For step a') and b') preferably the same applies as for step a) and b) as described above.

In an alternative preferred embodiment present invention relates to a method for preparing palbociclib of the present invention comprising the steps of
   a') providing palbociclib and/or protected palbociclib,
   b') dissolving palbociclib and/or protected palbociclib from step a') in mineral acid and/or organic acid,
   e') adding the solution from step b') to an aqueous, alkaline solution, and
   f') isolating palbociclib in crystalline form.

In alternative step a') palbociclib and/or protected palbociclib is provided. Palbociclib preferably refers to palbociclib in form of its free base. Protected palbociclib preferably refers to palbociclib, wherein the secondary amine of the piperazine residue is protected with a protecting group, in particular with a protecting group being hydrolizable under acidic conditions, in particular in aqueous hydrochloric acid. A preferred protecting group being hydrolizable under acidic conditions is tert-butyloxycarbonyl (Boc). In addition, palbociclib and/or protected palbociclib refer to the pharmaceutically acceptable salts, hydrates, solvates, and mixtures thereof.

In a preferred embodiment palbociclib in form of its free base is provided in alternative step a').

In an alternatively preferred embodiment Boc-protected palbociclib hydrochloride is provided in alternative step a').

In that embodiment (mineral acid in step b') preferably the same conditions with regard to mechanical movement apply as for step b) as described above.

In a preferred embodiment the mineral acid is selected from hydrochloric acid, hydrobromic acid, hydroiodic acid, sulfuric acid, phosphoric acid, and nitric acid. Preferred are hydrochloric acid, sulfuric acid, and phosphoric acid, in particular hydrochloric acid.

In a preferred embodiment the mineral acid can be present in form of an aqueous mineral acid.

It is preferred that the aqueous mineral acid is present as a 0.1N to 2N solution of the mineral acid in water.

In an alternative embodiment the mineral acid can additionally contain an organic acid, preferably an organic acid with 1 to 6 carbon atoms. Examples of organic acids are formic acid, acetic acid, propionic acid, oxalic acid and hexanoic acid.

Alternatively, instead of the mineral acid an organic acid, preferably capable of removing the protecting group from the protected palbociclib, can be used. In particular, the organic acid is capable of removing a Boc protecting group. Examples of such strong organic acids are formic acid, halogenated acetic acids, e.g. trifluoro acetic acid.

In a particularly preferred embodiment in step b') palbociclib and/or protected palbociclib from step a') are dissolved in aqueous mineral acid and organic acid, in particular in a mixture of aqueous hydrochloric acid and acetic acid.

In a preferred embodiment step b') can preferably be carried out at an elevated temperature. An elevated temperature corresponds to a temperature between 25° C. and the boiling point of the corresponding mixture, preferably between 40 and 80° C., in particular about 70° C.

It is further preferred that the step is carried out until the complete cleavage of the protecting group.

In case that in step b') the dissolution is carried out at an elevated temperature, said solution can preferably be cooled again to 25° C.

In case that in step b') palbociclib and/or protected palbociclib is dissolved in mineral acid and optionally organic acid, the optional steps c') and d') are preferably not carried out.

However, in case that in step b') palbociclib is dissolved in aqueous acetic acid, the optional step c') and d') are carried out. Preferably, for step c') the same applies as for step c) as described above.

Optional step d') is carried out, when palbociclib acetic acid adduct is isolated. Step d') includes dissolving, preferably completely dissolving palbociclib acetic acid adduct, in water. Step d') can preferably be carried out under mechanical movement, such as stirring. In a preferred embodiment, step d') includes stirring for 5 minutes to 1 hour, preferably 10 to 30 minutes. Step d') can preferably be carried out at 23° C. (room temperature).

In step e') the solution from step b') or the solution from step d') can preferably be added to an aqueous alkaline solution. Step e') can preferably be carried out under mechanical movement, such as stirring. Further, Step e') can preferably be carried at a temperature from 10° C. to 30° C., preferably 15° C. to 27° C., in particular 20° C. to 25° C. The alkaline solution can preferably have a pH-value from 9 to 15.

Further the alkaline solution can preferably contain an inorganic alkaline substance. An alkaline substance is a substance which, when added to water, raises the pH value from 7 to a pH value being higher than 7.

Examples of inorganic alkaline substances are hydroxides/oxides of alkaline metals, hydroxides/oxides of alkaline earth metals, and carbonates/bicarbonates of alkaline metals and of alkaline earth metals. Examples of alkaline metals are lithium, sodium and potassium. Examples of alkaline earth metals are magnesium and calcium.

In a preferred embodiment, the alkaline solution can preferably comprise an inorganic alkaline substance, preferably selected from sodium hydroxide, potassium hydroxide, sodium carbonate and potassium carbonate. More preferred is sodium hydroxide.

In a particularly preferred embodiment the alkaline solution is 0.1 to 2.0 n (normal), more preferably 0.5 to 1.5 n, in particular 0.8 to 1.2 n sodium hydroxide solution.

In step f') the isolation of palbociclib in crystalline form according to the present invention can preferably be carried out by filtering off the solid. Further, palbociclib in crystalline form can preferably be washed, preferably with water.

Subsequently, palbociclib in crystalline form can preferably be dried. Drying can preferably be carried out at a temperature of 15° C. to 40° C., preferably at 23° C. Alternatively or additionally, the drying can preferably be carried out under reduced pressure of 0.1 to 50 mbar, in particular 1 to 10 mbar.

As can be seen from the above, palbociclib in the crystalline form of the present invention is advantageously accessible by a process without the use of complex, time- and cost-intensive process steps.

The present invention furthermore relates to pharmaceutical compositions comprising the compounds of the invention, i.e. in particular palbociclib acetic acid adduct, in particular Form 1 and 2 of the palbociclib acetic acid adduct, and palbociclib in crystalline form, wherein the pharmaceutical compositons additionally contain at least one pharmaceutically acceptable excipient.

Pharmaceutically acceptable excipient(s) can for example be fillers, binders, glidants, disintegrants, lubricants, flow regulating agents and release agents. Suitable excipients are for example disclosed in "Lexikon der Hilfsstoffe fur Pharmazie, Kosmetik and angrenzende Gebiete", published by H. P. Fielder, $4^{th}$ Edition and "Handbook of Pharmaceutical Excipients", $3^{rd}$ Edition, published by A. H. Kibbe, American Pharmaceutical Association, Washington, USA, and Pharmaceutical Press, London.

The term filler generally means substances which serve to form the body of the tablet in the case of tablets with small amounts of active agent (e.g. less than 60% by weight). This means that fillers "dilute" the active agent(s) in order to produce an adequate tablet compression mixture. The normal purpose of fillers therefore is to obtain a suitable tablet size. Examples of preferred fillers are lactose, lactose derivatives, starch, starch derivatives, treated starch, chitin, cellulose and derivatives thereof, calcium phosphate, calcium hydrogen phosphate, sucrose, calcium carbonate, magnesium carbonate, magnesium oxide, maltodextrin, calcium sulphate, dextrates, dextrin and/or dextrose, and hydrogenated vegetable oil. Fillers can be present in an amount of 0 to 80% by weight, preferably in an amount of 10 to 60% by weight of the total weight of the composition.

A binder is generally a substance which is capable of increasing the strength of the resulting dosage form, especially the resulting tablets. Suitable binders are for example polyvinylpyrrolidone, hydroxypropyl cellulose, hydroxypropyl methyl-cellulose, methylcellulose, hydroxyethyl cellulose, sugars, dextran, corn starch.

Binders can be present in an amount of 0 to 30% by weight, preferably in an amount of 2 to 15% by weight of the total weight of the composition.

Glidants can be used to improve the flowability. Suitable glidants are for example alkaline earth metal salts of fatty acids, like stearic acid. The glidant can be present for example in an amount of 0 to 2% by weight, preferably in an amount of 0.5 to 1.5% by weight of the total weight of the composition.

Disintegrants are compounds which enhance the ability of the dosage form, preferably the ability of the tablet, to break into smaller fragments when in contact with a liquid, preferably water. Suitable disintegrants are for example croscarmellose sodium, sodium carboxymethyl starch, cross-linked polyvinylpyrrolidone (crospovidone), sodium carboxymethylglycolate and sodium bicarbonate. The disintegrant can be present in an amount of 0 to 20% by weight, preferably in an amount of 1 to 15% by weight of the total weight of the composition.

A suitable flow regulating agent is for example colloidal silica. The flow regulating agent can be present in an amount of 0 to 8% by weight, preferably in an amount of 0.1 to 3% by weight of the total weight of the composition.

A suitable release agent is for example talcum. The release agent can be present in an amount of 0 to 5% by weight, preferably in an amount of 0.5 to 3% by weight of the total weight of the composition.

The parmaceutical composition can preferably be further processed into an oral doasage form, such as a capsule or tablet.

In preferred embodiment the oral dosage form is a tablet.

In an alternative preferred embodiment the oral dosage form is a capsule, preferably a hard capsule, in particular a hard gelatine capsule. Alternatively preferred the capsule is a soft capsule, e.g. a soft gelatine capsule.

It is preferred that the oral dosage form is a hard capsule. Hard capsules known also as two-pieces capsules can be formed by two precast cylinders each being hemispherically sealed at one end, respectively.

The hard gelatine capsules can preferably have a volume from 0.02 to 1.37 ml, more preferably from 0.1 to 0.91 ml.

Hard capsules can preferably be produced using gelatine or other pharmaceutically acceptable materials, preferably polymers such as hydroxypropyl methylcellulose. The capsules may be dyed by adding dyes during the production process.

The preparation of hard capsules can preferably be carried out according to the Colton process in which pins are dipped into an aqueous gelatine or polymer solution such that the pins are covered with a thin film of gelatine or polymer wherein the film is further solidified and dried.

Hard gelatine capsules preferably comprise gelatine, water and optionally dye. It is preferred that hard gelatine capsules do not comprise further components, in particular no plasticizers.

The hard capsules can be preferably filled with liquid, semi-solid or solid pharmaceutical compositions.

It is alternatively preferred that the solid oral dosage form is a soft capsule, wherein the soft capsule comprises a shell and a fill matrix.

Preferably, the fill matrix contains or consists of the pharmaceutical composition. The shell preferably has a thickness of 0.2 to 1.8 mm. The oral dosage form, preferably a tablet or a capsule, more preferably a tablet, can preferably be coated, preferably film coated.

In the present invention the following three types of film coatings are possible:
  film coatings without affecting the release of the active ingredient,
  gastric juice-resistant film coatings,
  retard film coatings.

Generally, film coatings can be prepared by using film-forming agents, such as waxes, cellulose derivatives, poly (meth)acrylate, polyvinylpyrrolidone, polyvinyl acetate phthalate, and/or shellac or natural rubbers, such as carrageenan.

It is preferred that the present tablet is coated with a gastric juice-resistant film coating. Alternatively, a capsule comprising a gastric juice-resistant film coating can be used.

The gastric juice-resistant film coating preferably is a film coating, being stable in the pH range of about 0.7 to 3.0, which is supposed to be the pH-value of human gastric juice found in the stomach. However, in an environment with a pH value of 5 to 9, which is supposed to be present in the (small) intestine of the human body, the gastric juice-resistant film coating preferably dissolves and the drug can be released.

The gastric juice-resistant film coating (often also referred to as enteric coating) can comprise film-forming agents, for example fats, fatty acids, waxes, alginates, shellac, polyvinyl acetate phthalate, cellulose derivatives such as carboxy methyl ethyl cellulose, cellulose acetate succinate, cellulose acetate phthalate, hydroxy-propyl methyl cellulose phthalate, hydroxypropyl methyl cellulose acetate succinate, cellulose acetate trimellitate, and meth(acrylic)acid copolymers, such as methyl acrylate-methacrylic acid copolymers, methyl methacrylate-methacrylic acid copolymers and Eudragits (for example Eudragit® L30D, Eudragit® L, Eudragit® S).

The coating is preferably free of active ingredient. It is further preferred that the thickness of the coating is 10 µm to 2 mm, preferably from 50 to 500 µm.

The preferred coating may comprise a film-forming agent and one or more of the following: lubricant, surfactant, glidant, pigment and water.

The preferred coating according to an embodiment of the present invention can comprise, along with the film-forming agent, e.g. stearic acid as lubricant for plasticizing and dissolving the polymer, sodium lauryl sulfate as a surfactant for wetting and dispersing, talc as glidant, iron oxide yellow and/or titanium oxide as pigment(s) and optionally purified water.

The present pharmaceutical composition and/or the oral dosage form of the present invention can be prepared by the methods well-known to a person skilled in the art, such as dry and wet granulation and direct compression.

In a preferred embodiment, the pharmaceutical composition and/or the oral dosage form can be administered one to three times a day, preferably once or twice a day, more preferably once a day.

The present invention further relates to compounds of the invention, in particular palbociclib acetic acid adduct, in particular Form 1 and Form 2 of said adduct, and palbociclib in the crystalline form of the present invention, for use in the treatment of cancer, preferably for use in the treatment of breast cancer.

The term "cancer" includes both solid tumors and hematological malignancies. Cancers include, but are not limited to, breast cancer, ovarian cancer, cervical cancer, endometrial cancer, prostate cancer, testicular cancer, pancreatic cancer, esophageal cancer, head and neck cancer, gastric cancer, bladder cancer, lung cancer (e.g., adenocarcinoma, NSCLC and SCLC), bone cancer (e.g., osteosarcoma), colon cancer, rectal cancer, thyroid cancer, brain and central nervous system cancers, glioblastoma, neuroblastoma, neuroendocrine cancer, rhabdoid cancer, keratoacanthoma, epidermoid carcinoma, seminoma, melanoma, sarcoma (e.g., liposarcoma), bladder cancer, liver cancer (e.g., hepatocellular carcinoma), kidney cancer (e.g., renal cell carcinoma), myeloid disorders (e.g., AML, CML, myelodysplastic syndrome and promyelocytic leukemia), and lymphoid disorders (e.g., leukemia, multiple myeloma, mantle cell lymphoma, ALL, CLL, B-cell lymphoma, T-cell lymphoma, Hodgkin's lymphoma, non-Hodgkin's lymphoma, hairy cell lymphoma).

Further, the present invention is directed to a method of treating and/or preventing cancer, preferably treating and/or preventing breast cancer, comprising administering to a subject in need thereof a therapeutically effective amount of the compounds of the invention or the pharmaceutical composition according to the present invention.

EXAMPLES

Analytical Methods
X-ray Powder Diffraction

The samples were measured on a D8 Advance powder X-ray diffractometer (Bruker AXS, Karlsruhe, Germany) in a rotating PMMA sample holder (diameter: 25 mm; depth:

1 mm) in reflection mode (Bragg-Brentano geometry). Conditions of the measurements are summarized in the following table. Raw data were analyzed with the program EVA (Bruker AXS, Karlsruhe, Germany). Figures were prepared from diffractograms without background subtraction and without K$\alpha_2$ stripping. Relative intensities in peak lists were determined after background subtraction.

Conditions for Powder Diffraction Measurements

| | |
|---|---|
| Radiation | Cu K$\alpha_1$/$\alpha_2$ (weighted average: 1.54187 Å) |
| Source | 34 kV/40 mA |
| Detector | Vantec-1 (electronic window: 3°) |
| K$\beta$ filter | Ni (diffracted beam) |
| measuring circle diameter | 435 mm |
| detector window slit | 12 mm |
| anti-scatter slit (diffracted beam) | 8 mm |
| divergence slit | v6.00 (variable) |
| Soller slit (incident/diffracted beam) | 2.5° |
| 2θ range | 2° < 2θ < 55° |
| step size | 0.016 |
| step time | 0.2 s |

Differential Scanning Calorimetry

The samples were placed in sealed aluminium crucibles (40 μL) with perforated lids (one hole in the centre, made by puncturing with a cannula of 0.6 mm diameter). The measured DSC curves are displayed as a function of the program temperature (proportional to the measurement time). Characteristic temperature values of DSC signals (onset/endset temperature, peak maximum) were determined from the sample temperature, which may deviate from the program temperature. Signals with positive area correspond to endothermic events.

Apparatus: Mettler-Toledo DSC 822E coupled with a Mettler-Toledo Gas-Flow-Controller TS0800GC1 (Mettler-Toledo GmbH, Gießen, Germany)

Aluminium crucible: 40 μL (with perforated lid)

Temperature range: 30° C. to 350° C.

Heating rate: 10° C./min

Nitrogen flow: 50 mL/min

Software: STARe Version 12.00a

Interpretation: Endothermic mode

Thermogravimetry

The samples were placed in open aluminum crucibles (40 μL). The measured weight and heat current curves are displayed as a function of the program temperature (proportional to the measurement time). Heat current signals with positive area correspond to endothermic events.

Apparatus: Mettler-Toledo TGA/DSC1 (Mettler-Toledo GmbH, Gießen, Germany)

Aluminium crucible: 40 μL (open)

Temperature range: 25° C. to 350° C.

Heating rate: 10° C./min

Nitrogen flow: 50 mL/min

Software: STARe Version 11.00

Nuclear Magnetic Resonance Spectroscopy

Instrument: Varian Mercury 400 Plus NMR Spectrometer, Oxford AS, 400 MHz.

Dynamic Vapor Sorption Measurement

Vapour sorption experiments were performed in the instrument SPSx-1 μ (Projekt Messtechnik, Ulm, Germany) at a temperature of 25° C., using the humidity cycles specified below:

| Cycle No. | rel. humidity (% RH) start value | rel. humidity (% RH) end value | Number of steps | Time (h) | Comments |
|---|---|---|---|---|---|
| 1 | 40 | 0 | 4 | | |
| 2 | 5 | 65 | 6 | | |
| 3 | 75 | 75 | 1 | 24 h | To investigate the absorption of water at the upper humidity level during stress conditions |
| 4 | 85 | 95 | 1 | | |
| 5 | 90 | 0 | 9 | | |
| 6 | 5 | 35 | 3 | | |

Solubility Determination

Approximately 200 mg (exactly weighed) test substance was weighed into a glass vial, followed by addition of 2 mL solvent (water, 0.01M HCl, 20 mM NaOAc/HOAc pH 4.5, 50 mM KH$_2$PO$_4$ pH 6.8). A stirring bar was added, the vial was fixed in a block heater at 37° C. and the suspension was stirred with approximately 250 rpm. After 15 min and 1 hour samples were withdrawn, filtered through a 0.2 μm disposable filter, diluted with solvent and quantified by UHPLC/UV.

Solubilities in organic solvents (methanol, acetone, chloroform, DMSO) were determined similarly at room temperature with the difference that the suspensions were not stirred but treated with a vortex mixer for 20 s.

Starting Material

Palbociclib Form A as described in WO 2014/128588 A1 was used as starting material.

Example 1

Palbociclib Acetic Acid Adduct Form 1

Palbociclib (1.72 g) was dissolved in a mixture of glacial acetic acid (5 mL) and deionized water (5 mL). The solution was filtered through a folded filter and the solvents were removed on a rotary evaporator at 85 mbar/90° C. bath temperature. The resulting solid was triturated to a powder, which was further dried on the rotary evaporator at 85 mbar/90° C. bath temperature for 4 h. A yellow-brown powder was obtained.

Yield: 1.47 g (75%)

XRPD: 1$^{st}$ priority reflections 8.7, 10.0, 11.6, 13.4 and 19.1°2 θ 2$^{nd}$ priority reflections 4.5, 7.8, 16.1, 17.4 and 21.7°2 θ

$^1$H-NMR (CD$_3$OD/D$_2$O 1:1.13 [v/v]) [δ ppm]: 1.66 (m, 2H, CH), 1.81-2.02 (m, 7H, CH+CH$_3$COO), 2.27 (m, 2H, CH), 2.35 (s, 3H, CH$_3$), 2.49 (s, 3H, CH$_3$), 3.33 (m, 4H, piperazine-CH$_2$), 3.38 (m, 4H, piperazine-CH$_2$), 5.87 (quintet, 1H, J=8.9 Hz, CH), 7.51 (dd, 1H, J$_1$=9.2 Hz, J$_2$=2.9 Hz, pyridine-CH), 7.94 (d, 1H, J=9.0 Hz, pyridine-CH), 8.05 (d, 1H, J=2.7 Hz, pyridine-CH), 8.93 (s, 1H, pyrimidine-CH)

DSC: endotherms (onset T):186° C., 261° C., 275° C. (FIG. 4)

As can be seen from the TGA-thermogram in FIG. 5 acetic acid evaporates between 100° and 220° C. at a heating rate of 10° C./min. The observed weight loss amounted to 11.7%, wherein the theoretical value for 1:1 stoichiometry (palbociclib: acetic acid) is 11.8%. The results of dynamic vapor sorption measurements are shown in FIG. 6. The weight curves feature no steps which would be indicative for the formation of stoichiometrically defined hydrated forms, and the sample weight after the measurement was almost unchanged (−0.5%). The diffractogram after DVS measurement was practically identical with the initial one.

Example 2

Palbociclib Acetic Acid Adduct Form 2

Palbociclib (7 g) was dissolved in a mixture of glacial acetic acid (20 mL) and water (20 mL). The solution was filtered through a folded filter and the solvents were removed on a rotary evaporator at 60 mbar/50° C. bath temperature. The remaining solid was further dried 12 h at room temperature under fine vacuum (rotary vane pump, approx. 0.001 mbar) and further at 80° C./8 mbar 24 hours. A yellow powder was obtained.
Yield: 7.4 g (93%)
XRPD: $1^{st}$ priority reflections 9.2, 10.9, 13.1, 13.8 and 23.0°2 θ $2^{nd}$ priority reflections 4.6, 17.0, 19.5, 20.0 and 21.5°2 θ
DSC: endotherms (onset T):162° C., 260° C. (FIG. 7)
As it can be seen from the TGA-thermogram in FIG. 8 acetic acid evaporates between 120° and 220° C. at a heating rate of 10° C./min. The observed weight loss amounted to 11.2%.

Example 3

Palbociclib in Crystalline Form

Palbociclib acetic acid solvate (250 mg) was dissolved in deionized water (9 mL). The clear solution was added dropwise within 7 minutes to a mixture of aqueous 1N NaOH solution (0.6 mL) and deionized water (8 mL) at room temperature under magnetic stirring. A yellow solid precipitated immediately. The mixture was further stirred for 15 min, then it was stored 2 hours at room temperature without stirring. The solid was isolated by filtration, washed with deionized water (2×20 mL) and dried 3 hours in open atmosphere at room temperature, then 1 hour in dynamic vacuum (2 mbar) at room temperature. A yellow powder was obtained.
Yield: 156 mg (71%)

Example 3'

Palbociclib in Crystalline Form

Palbociclib (5 g) was dissolved in glacial acetic acid (20 mL). Deionized water (20 mL) was added and the solution was filtered through a folded filter. The clear solution was added dropwise to aqueous 1N NaOH solution (384 mL) under stirring at room temperature. A yellow solid precipitated immediately. After complete addition, the mixture was further stirred for 30 minutes. The solid was then isolated by filtration, washed with deionized water (2×30 mL) and dried in dynamic vacuum (5 mbar) at room temperature for 2 days. A yellow powder was obtained.
Yield: 4.6 g (92%)

Example 3"

Palbociclib in Crystalline Form

Palbociclib (0.5 g, 1.1 mmol) was stirred 10 min at room temperature (23° C.) in a mixture of water (5 mL) and 1.12 mL 1N HCl (1.0 equivalent). The essentially clear solution was filtered through a folded filter. The filtrate was initially clear, but turns slightly turbid within 5 minutes. This suspension was added dropwise to a mixture of 1N NaOH (1.3 mL) and water (5 mL) under stirring at RT (23° C.). A yellow solid precipitated, the mixture was further stirred for 30 minutes, then stored at room temperature (23° C.) for 1 hour. The solid was isolated by filtration, washed with water, and dried at 2 mbar/room temperature (23° C.) for 2 hours.
Yield: 254 mg (51%).

Example 3'''

Palbociclib in Crystalline Form by Use of Protected Palbociclib as Educt

4-[6-(6-Acetyl-8-cyclopentyl-5-methyl-7-oxo-7,8-dihydro-pyrido[2,3-d]pyrimidin-2-ylamino)-pyridin-3-yl]-piperazine-1-carboxylic acid tert-butyl ester hydrochloride (Boc-protected palbociclib hydrochloride) (1.0 g, 1.7 mmol) was suspended in a mixture of water (5 ml) and acetic acid (4 ml). 0.83 ml of HCl 32% solution (8.6 mmol, 5.0 eq.) were added dropwise, the mixture was heated to 70° C. and stirred for 2.5 hours (until completion). After cooling to 50° C., 10 ml of water were added followed by 3.4 ml of an aqueous 2N NaOH solution. The yellow solution was cooled to 23° C. (room temperature), filtered through a 1 µm filter and added dropwise within 5 min to an aqueous 2N NaOH solution (37.8 mL) at 23° C. (room temperature) under magnetic stirring. A yellow solid precipitated immediately. The mixture was further stirred for 15 min, then it was stored for 20 min at 23° C. (room temperature) without stirring. The solid was isolated by filtration, washed with deionized water (3×20 mL) and dried at 50° C./10 mbar for 72 h to give a yellow solid.
Yield: 684 mg (89.3%)
The following data are identical in Examples 3, 3', 3" and 3'''
XRPD: $1^{st}$ priority reflections 6.0, 10.9, 12.8, 16.3 and 19.7°2 θ $2^{nd}$ priority reflections 6.6, 19.4, 22.0, 22.5 and 26.64°2 θ
$^1$H-NMR (DMSO-D$_6$) [δ ppm]: 1.57 (m, 2H, CH), 1.75 (m, 2H, CH), 1.86 (m, 2H, CH), 2.23 (m, 2H, CH), 2.29 (s, 3H, CH$_3$), 2.40 (s, 3H, CH$_3$), 2.83 (m, 4H, piperazine-CH$_2$), 3.04 (m, 4H, piperazine-CH$_2$), 5.80 (quintet, 1H, J=8.9 Hz, CH), 7.42 (dd, 1H, J$_1$=9.0 Hz, J$_2$ =3.1 Hz, pyridine-CH), 7.82 (d, 1H, J=9.0 Hz, pyridine-CH), 8.02 (d, 1H, J=2.7 Hz, pyridine-CH), 8.93 (s, 1H, pyrimidine-CH), 10.05 (s, 1H, NH)
DSC: endotherms (onset T): 98° C., 271° C. (FIG. 9)
The DSC thermogram features two endothermic peaks at 103° C. (onset: 98° C.) and 272° C. (onset 271° C.). In the DSC thermogram the peak at 103° C. does not correspond to loss of residual water. In fact cyclic DSC measurements (FIG. 10) indicate that this peak corresponds to a reversible transformation. The TGA thermogram (FIG. 11) shows only a marginal weight loss of 0.2% until 200° C. Hence, the product is an anhydrous form.
Results of dynamic vapor sorption measurements are shown in FIG. 12. There are no clear steps in the weight curves which would be indicative for the formation of stoichiometrically defined hydrates. The maximum water uptake was 1.3% and the sample weight after the measurement was almost unchanged (−0.2%). The diffractogram after DVS measurement was practically identical with the initial one.

Results
Solubility:

Solubilities of palbociclib acetic acid adduct Form 1, present palbociclib in crystalline form and palbociclib Form A in aqueous solvents at 37° C. are shown in the following Table 1.

TABLE 1

Solubilities of different palbociclib forms in aqueous solvents at 37° C.

| | Palbociclib acetic acid adduct Form 1 | | Palbociclib in present crystalline Form | | Palbociclib Form A | |
|---|---|---|---|---|---|---|
| | 15 min | 60 min | 15 min | 60 min | 15 min | 60 min |
| Water | 34.9 | 36.3 | 0.0 | 0.0 | 0.0 | 0.0 |
| 0.01M HCl | 41.4 | 42.0 | 4.2 | 4.3 | 3.1 | 3.0 |
| 20 mM NaOAc/HOAc | 15.9 | 16.0 | 16.2 | 15.0 | 12.4 | 11.7 |
| 50 mM KH$_2$PO$_4$ | 8.1 | 5.0 | 0.1 | 0.1 | 0.0 | 0.0 |

Form A and present crystalline palbociclib are insoluble in water and in 50 mM KH$_2$PO$_4$ solution. In 20 mM NaOAc/HOAc solution and in 0.01M HCl they are sparingly soluble, whereby present crystalline palbociclib is slightly better soluble in both cases. In contrast, palbociclib acetic acid adduct Form 1 shows good solubility in water and in 0.01M HCl.

Solubilities of palbociclib acetic acid adduct Form 1, present crystalline palbociclib and palbociclib Form A in different organic solvents aqueous solvents at 23° C. (room temerature) are shown in the follwing Table 2.

TABLE 2

Solubilities of different palbociclib forms in organic solvents at 23° C. (room temperature)

| | Palbociclib in present crystalline form | Palbociclib Form A | Palbociclib acetic acid adduct Form 1 |
|---|---|---|---|
| methanol | 1.2 | 0.5 | |
| Acetone | 0.5 | 0.2 | |
| chloroform | 86.1 | 48.7 | 7.3 |
| dimethyl sulfoxide | 4.0 | 1.5 | |

The solubility of present palbociclib in crystalline form in chloroform, methanol, acetone, and DMSO is 1.8 to 2.7 times higher than for Form A.

SUMMARY

A method for the preparation of palbociclib in crystalline form has been achieved. The solubility of palbociclib in crystalline form in aqueous solvents is comparable to that of Form A. However, the solubility of palbociclib in crystalline form in four examined organic solvents is 1.8 to 2.7 times higher than the one of palbociclib Form A. Further, new palbociclib acetic acid adduct Form 1 and Form 2 were prepared, which can be used as an intermediate in the formation of palbociclib in crystalline form. The palbociclib acetic acid adduct Form 1 and Form 2 is a crystalline solid, which is well soluble in water and in 0.01M HCl.

The invention claimed is:

1. Crystalline palbociclib characterized by a powder X-ray diffraction pattern comprising diffraction peaks at 2θ values of 6.0°±0.2°, 10.9°±0.2°, 12.8°±0.2°, 16.3°±0.2° and 19.7°±0.2°.

2. The crystalline palbociclib according to claim 1, wherein the crystalline palbociclib is further characterized by a powder X-ray diffraction pattern comprising one or more additional diffraction peaks at 2θ values of 6.6°±0.2°, 19.4°±0.2°, 22.0°±0.2°, 22.5°±0.2° and 26.6°±0.2°.

3. A pharmaceutical composition comprising crystalline palbociclib according to claim 1 and at least one pharmaceutically acceptable excipient.

4. A method for treating breast cancer in a subject, comprising administering to a subject in need thereof a therapeutically effective amount of crystalline palbociclib according to claim 1.

5. A process for preparing crystalline palbociclib according to claim 1, wherein the process comprises the following steps:
   a) dissolving palbociclib in aqueous acetic acid or a mineral acid selected from the group consisting of hydrochloric acid, hydrobromic acid, hydroiodic acid, sulfuric acid, phosphoric acid and nitric acid;
   b) optionally isolating palbociclib acetic acid adduct;
   c) optionally dissolving palbociclib acetic acid adduct in water;
   d) adding the solution of step a) or step c) to an alkaline aqueous solution; and
   e) isolating crystalline palbociclib.

6. The process according to claim 5, wherein the base in the alkaline aqueous solution is selected from the group consisting of sodium hydroxide, potassium hydroxide, sodium carbonate and potassium carbonate.

7. A process for preparing crystalline palbociclib according to claim 1, wherein the process comprises the following steps:
   a) dissolving palbociclib in an organic acid selected from the group consisting of formic acid, acetic acid, propionic acid, oxalic acid and hexanoic acid;
   b) adding the solution of step a) to an alkaline aqueous solution; and
   c) isolating crystalline palbociclib.

* * * * *